(12) United States Patent
Johnson et al.

(10) Patent No.: US 7,556,930 B2
(45) Date of Patent: Jul. 7, 2009

(54) CD39L3 AND ITS ROLE IN DIABETES

(75) Inventors: Jeffrey D. Johnson, Moraga, CA (US);
Yuko Terasawa, Campbell, CA (US);
Maria E. Wilson, San Francisco, CA (US)

(73) Assignee: Metabolex Inc., Hayward, CA (US)

( * ) Notice: Subject to any disclaimer, the term of this patent is extended or adjusted under 35 U.S.C. 154(b) by 302 days.

(21) Appl. No.: 11/402,142

(22) Filed: Apr. 10, 2006

(65) Prior Publication Data

US 2006/0246006 A1    Nov. 2, 2006

Related U.S. Application Data

(60) Provisional application No. 60/672,840, filed on Apr. 18, 2005.

(51) Int. Cl.
*G01N 33/53* (2006.01)
(52) U.S. Cl. .................................................. 435/7.2
(58) Field of Classification Search .................. None
See application file for complete search history.

(56) References Cited

U.S. PATENT DOCUMENTS

| | | | |
|---|---|---|---|
| 6,828,423 B1 * | 12/2004 | Chadwick et al. | 530/387.1 |
| 2003/0087247 A1 | 5/2003 | Kumamoto et al. | |
| 2003/0175752 A1 | 9/2003 | Ford et al. | |

OTHER PUBLICATIONS

Chadwick, B.P. et al.; "The CD39-like gene family: Identification of three new human members (CD39L2, CD39L3, and CD39L4), their murine homologues, and a member of the gene family from *Drosophila melanogaster*"; 1998, *Genomics*, vol. 50, No. 3, pp. 357-367.

Fernandez-Alvarez, J. et al.; "P2 Receptor Agonists Stimulate Insulin Release from Human Pancreatic Islets"; 2001, *Pancreas.*, vol. 22, No. 1, pp. 69-71.

Gendron, F.P. et al.; "Purine signaling and potential new therapeutic approach: possible outcomes of NTPDase inhibition"; 2002, *Curr. Drug Targets*, vol. 3, No. 3, pp. 229-245.

Geschwind, J.F. et al.; "Selective Activation of Ca2+ influx by extracellular ATP in a Pancreatic Beta-cell line (HIT)"; 1989, *Biochim Biophys Acta*, vol. 1012, No. 1, pp. 107-115.

Lavoie, E.G. et al.; "Cloning and characterization of mouse nucleoside triphosphate diphosphohydrolase-3"; 2004, *Biochem. Pharmacol.*, vol. 67, No. 10, pp. 1917-1926.

Lunkes, Gilberto Inacio et al.; "Enzymes that hydrolyze adenine nucleotides in diabetes and associated pathologies"; 2003, *Thrombosis Research*, vol. 109, pp. 189-194.

Smith, T.M. et al.; "Cloning, sequencing, and expression of a human brain ecto-apyrase related to both the ecto-ATPases and CD39 ecto-apyrases1"; 1998, *Biochem. Biophys. Acta*, vol. 1386, No. 1, pp. 65-78.

* cited by examiner

*Primary Examiner*—Michael Pak
(74) *Attorney, Agent, or Firm*—Townsend and Townsend and Crew LLP

(57) ABSTRACT

The present invention provides for methods and compositions related to the involvement of CD39L3 in insulin production.

6 Claims, 6 Drawing Sheets

CD39L3 AND ITS ROLE IN DIABETES

CROSS-REFERENCE TO RELATED PATENT APPLICATIONS

The present application claims benefit of priority to U.S. Provisional Patent Application No. 60/672,840, filed Apr. 18, 2005, which is incorporated by reference for all purposes.

BACKGROUND OF THE INVENTION

Diabetes mellitus can be divided into two clinical syndromes, Type 1 and Type 2 diabetes mellitus. Type 1, or insulin-dependent diabetes mellitus (IDDM), is a chronic autoimmune disease characterized by the extensive loss of beta cells in the pancreatic Islets of Langerhans, which produce insulin. As these cells are progressively destroyed, the amount of secreted insulin decreases, eventually leading to hyperglycemia (abnormally high level of glucose in the blood) when the amount of secreted insulin drops below the level required for euglycemia (normal blood glucose level). Although the exact trigger for this immune response is not known, patients with IDDM have high levels of antibodies against pancreatic beta cells. However, not all patients with high levels of these antibodies develop IDDM.

Type 2 diabetes (also referred to as non-insulin dependent diabetes mellitus (NIDDM)) develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing their insulin output. Over time, these cells become unable to produce enough insulin to maintain normal glucose levels, indicating progression to Type 2 diabetes.

Type 2 diabetes is brought on by a combination of poorly understood genetic and acquired risk factors—including a high-fat diet, lack of exercise, and aging. Worldwide, Type 2 diabetes has become an epidemic, driven by increases in obesity and a sedentary lifestyle, widespread adoption of western dietary habits, and the general aging of the populations in many countries. In 1985, an estimated 30 million people worldwide had diabetes—by 2000, this figure had increased 5-fold, to an estimated 154 million people. The number of people with diabetes is expected to double between now and 2025, to about 300 million.

Type 2 diabetes is a complex disease characterized by defects in glucose and lipid metabolism. Typically there are perturbations in many metabolic parameters including increases in fasting plasma glucose levels, free fatty acid levels and triglyceride levels, as well as a decrease in the ratio of HDL/LDL. As discussed above, one of the principal underlying causes of diabetes is the inability of beta cells to produce sufficient insulin to maintain glucose levels. Therefore, an important therapeutic goal in the treatment of diabetes is therefore to increase insulin production. The present invention addresses this and other problems.

BRIEF SUMMARY OF THE INVENTION

The present invention provides methods for identifying an agent for treating a diabetic or pre-diabetic individual. In some embodiments, the methods comprise the steps of:
(i) contacting an agent to a CD39L3 polypeptide at least 95% identical to SEQ ID NO:2, wherein the polypeptide has nucleotide hydrolysis activity;
(ii) selecting an agent that reduces the activity of the polypeptide; and
(iii) testing the effect of the selected agent on glucose-stimulated insulin expression of a cell, thereby identifying an agent for treating a diabetic or pre-diabetic individual.

In some embodiments, the polypeptide is expressed on a cell and the contacting step (i) comprises contacting the cell with the agent.

In some embodiments, a membrane fraction comprises the polypeptide.

In some embodiments, the activity of the polypeptide is measured by detecting free phosphate in the mixture.

In some embodiments, the polypeptide comprises SEQ ID NO:2.

In some embodiments, the method further comprises testing the effect of the selected agent on the activity of a second ectoATPase other than CD39L3 and selecting an agent that does not reduce the activity of the second ectoATPase.

The present invention also provides methods of treating a diabetic or pre-diabetic animal. In some embodiments, the methods comprise administering to the animal a therapeutically effective amount of an agent that reduces the nucleotide hydrolysis activity of a CD39L3 polypeptide comprising SEQ ID NO:2.

In some embodiments, the agent is identified by a method comprising the steps of:
(i) contacting an agent to a CD39L3 polypeptide at least 95% identical to SEQ ID NO:2, wherein the polypeptide has nucleotide hydrolysis activity;
(ii) selecting an agent that reduces the activity of the polypeptide; and
(iii) testing the effect of the selected agent on glucose-stimulated insulin expression of a cell.

In some embodiments, the agent does not reduce the activity of NTDPase 1, 2, 4, 5, 6, 7, or 8 in the individual.

In some embodiments, the agent is an antibody that binds to the CD39L3 polypeptide.

In some embodiments, the antibody is a monoclonal antibody.

In some embodiments, wherein the animal is a human.

The present invention also provides methods for detecting β-cell mass or function in an individual. In some embodiments, the methods comprise:

detecting the quantity of a CD39L3 polypeptide at least 95% identical to SEQ ID NO:2 or a specific fragment thereof in a bodily fluid of the individual; and comparing the quantity of the polypeptide to the amount of CD39L3 polypeptide in the bodily fluid of a lean non-diabetic individual, wherein the quantity of CD39L3 in the bodily fluid is proportional to the relative β-cell mass and/or function in an individual.

In some embodiments, the individual is suspected of being diabetic or pre-diabetic.

The present invention also provides methods of in vivo imaging β-cells of an individual. In some embodiments, the method comprises:

detecting cells expressing a CD39L3 polypeptide at least 95% identical to SEQ ID NO:2, or a transcript encoding the polypeptide, by contacting the individual with a detectably-labeled reagent that binds to the CD39L3 polypeptide; and generating a representational image of the cells expressing the polypeptide.

In some embodiments, the reagent comprises an antibody that binds to the CD39L3 polypeptide.

In some embodiments, wherein the reagent is introduced into blood of the individual.

In some embodiments, the representational image of the cells is displayed on a computer monitor.

DEFINITIONS

"CD39L3" is a member the E-NTPDase family of transmembrane proteins that catalyzes the hydrolysis γ and/or β phosphate residues of nucleotides. See, e.g., Smith, T. M. and Kirley, T. L., *Biochim. Biophys. Acta* 1386 (1), 65-78 (1998); Chadwick, B. P. and Frischauf, A. M., *Genomics* 50 (3), 357-367 (1998); Lavoie et al., *Biochem Pharmacol.* 67(10): 1917-26 (2004). CD39L3 is expressed on the plasma membrane, bounded by two transmembrane domains with the catalytic region facing the extracellular milieu. As used herein, "CD39L3 polypeptide" refers to naturally-occurring sequences such as provided in SEQ ID NO:2 as well as non-natural variants that are substantially identical to SEQ ID NO:2 and have nucleotide hydrolysis activity as well as fragments of such naturally-occurring sequences or non-natural variants having nucleotide hydrolysis activity. CD39L3 polypeptides are also referred to as ENTPD3, NTPDase3, and HB6 in the scientific literature.

The full length human CD39L3 cDNA has 1590 base pairs (Accession number: NM_001248), which was originally cloned from a human brain library. The CD39L3 protein product consists of 529 amino acids (Accession number: NP_001239). CD39L3 is similar to E-type nucleotidases (NTPases) and contains four highly conserved regions of homology termed apyrase conserved regions I-IV (ACRs). See, e.g., Chadwick, B. P. and Frischauf, A. M., *Genomics* 50 (3), 357-367 (1998); Lavoie et al., *Biochem Pharmacol.* 67(10):1917-26 (2004); Yang et al., *Biochemistry* 40(13): 3943-50 (2001); Smith et al., *Biochemistry* 38(1):321-8 (1999); Hicks-Berger, et al., *Biochim Biophys Acta.* 1547(1): 72-81 (2001); Kirley et al., *Arch Biochem Biophys.* 395(1): 94-102 (2001).

A person is "predisposed for diabetes" when the person is at high risk for developing diabetes. A number of risk factors are known to those of skill in the art and include: genetic factors (e.g., carrying alleles that result in a higher occurrence of diabetes than in the average population or having parents or siblings with diabetes); overweight (e.g., body mass index (BMI) greater or equal to 25 kg/m$^2$); habitual physical inactivity, race/ethnicity (e.g., African-American, Hispanic-American, Native Americans, Asian-Americans, Pacific Islanders); previously identified impaired fasting glucose or impaired glucose tolerance, hypertension (e.g., greater or equal to 140/90 mmHg in adults); HDL cholesterol greater or equal to 35 mg/dl; triglyceride levels greater or equal to 250 mg/dl; a history of gestational diabetes or delivery of a baby over nine pounds; and/or polycystic ovary syndrome. See, e.g., "Report of the Expert Committee on the Diagnosis and Classification of Diabetes Mellitus" and "Screening for Diabetes" *Diabetes Care* 25(1): S5-S24 (2002).

A "pre-diabetic individual" refers to an adult with a fasting blood glucose level greater than 110 mg/dl but less than 126 mg/dl or a 2 hour PG reading of greater than 140 mg/dl but less than 200 mg/dl. A "diabetic individual" refers to an adult with a fasting blood glucose level greater than 126 mg/dl or a 2 hour PG reading of greater than 200 mg/dl.

A "lean individual" refers to an adult with a fasting blood glucose level less than 110 mg/dl or a 2 hour PG reading of 140 mg/dl. "Fasting" refers to no caloric intake for at least 8 hours. A "2 hour PG" refers to the level of blood glucose after challenging a patient to a glucose load containing the equivalent of 75 g anhydrous glucose dissolved in water. The overall test is generally referred to as an oral glucose tolerance test (OGTT). See, e.g., *Diabetes Care*, Supplement 2002, American Diabetes Association: Clinical Practice Recommendations 2002. The level of a polypeptide in a lean individual can be a reading from a single individual, but is typically a statistically relevant average from a group of lean individuals. The level of a polypeptide in a lean individual can be represented by a value, for example in a computer program.

A "specific fragment" of a particular polypeptide in a sample, as used herein, refers to a fragment that is sufficiently large to distinguish the fragment as derived from the particular polypeptide and as not a fragment from other proteins in the sample. A specific fragment can comprise, e.g., at least 10, 20, 30, 50, 75, 100, 150 or more contiguous amino acids of a CD39L3 polypeptide. In some cases, the fragments lack the transmembrane domains of full-length CD39L3. Thus in some embodiments, the fragments are as large as 439 amino acids, i.e., the length of the protein without the transmembrane domains.

"Antibody," as used herein, refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv, humanized anibodies, chimeric antibodies, etc.).

The term "isolated," when applied to a nucleic acid or protein, denotes that the nucleic acid or protein is free of at least cellular components with which it is associated in the natural state.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified in naturally-occurring cells, e.g., hydroxyproline, γ-carboxyglutamate, and O-phosphoserine. Amino acid "analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

With reference to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same. The term "substantially identical" refers to two or more sequences that have a specified percentage of amino acid residues or nucleotides that are the same (i.e., 60% identity, optionally 65%, 70%, 75%, 80%, 85%, 90%, or 95% identity over a specified region or over an entire sequence when no region is specified), when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. The present invention provides polynucleotides and polypeptides substantially identical to SEQ ID NOs:1 or 2, respectively.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Antagonists" of CD39L3 activity are used to refer to agents that, e.g., partially or totally block any activity of CD39L3 including, e.g., nucleoside hydrolysis activity. Samples or assays comprising CD39L3 that are treated with a potential antagonist, can be compared to control samples without the antagonist to examine the extent of effect. Control samples (untreated with antagonists) are assigned a relative CD39L3 activity value of 100%. Antagonism of CD39L3 is achieved when the CD39L3 activity value relative to the control is less than about 80%, optionally 50% or 25, 10%, 5% or 1%.

DETAILED DESCRIPTION OF THE INVENTION

I. Introduction

Figure 1:
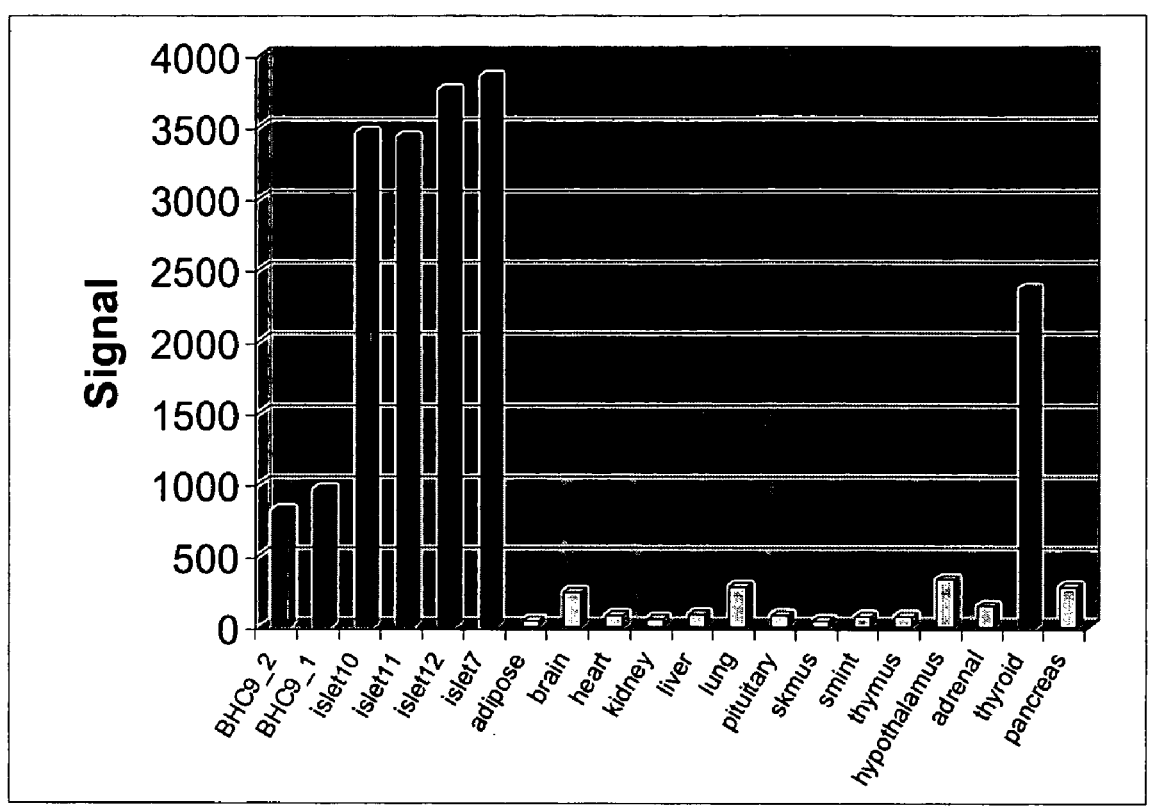
FIG. 1 illustrates expression analysis from a custom mouse islet chip profile for gene representing CD39L3. The samples analyzed were: βHC9 cells, islets, adipose, brain, heart, kidney, liver, lung, pituitary, skeletal muscle, small intestine, thymus, hypothalamus, adrenal, thyroid, and pancreas. The gene was called present according to the Affymetrix analysis software in all four islet samples, in two βHC9 cells, and in the thyroid gland and absent in all other non-islet samples examined.

The present invention surprisingly demonstrates that expression of CD39L3 (also referred to in the scientific literature as ENTPD3, NTPDase3, HB6 and sometimes by the generic term "ectoATPase") in insulin-producing cells impairs secretion of insulin. Accordingly, methods of identifying antagonists of CD39L3, as well as methods of stimulating insulin production by antagonizing CD39L3, are provided. The discovery of the effect of CD39L3 on insulin production, and its expression in islet cells (where insulin is produced), also allows for the determination of β-cell mass and/or function by detecting CD39L3.

This invention involves routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994-2004)).

II. Identification of Modulators of CD39L3

Antagonists of CD39L3 (i.e., agents that reduce or prevent activity of CD39L3) are useful for stimulating insulin production in individuals, including individuals with type 2 diabetes or individuals with insulin resistance (i.e., pre-diabetic individuals) or other conditions in which it is beneficial to increase insulin production.

A. CD39L3 Antagonists

CD39L3 antagonists can be any small chemical compound, or a biological entity, such as a protein (including, e.g., an antibody), sugar, nucleic acid or lipid.

A wide variety of methods can be used to identify agents that antagonize CD39L3. Typically, test compounds will be small chemical molecules and/or peptides. Essentially any chemical compound can be used as a potential modulator (e.g., antagonist) in the assays of the invention, although most often compounds that can be dissolved in aqueous or organic (especially DMSO-based) solutions are used. The assays can be designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

B. CD39L3

CD39L3 polypeptides for use in the invention include polypeptides comprising:

(i) the naturally-occurring CD39L3 amino acid sequence (e.g., human (e.g., SEQ ID NO:2) or other animal orthologs);

(ii) amino acid sequences substantially identical to a naturally-occurring amino acid sequence (e.g., other naturally-occurring or human-modified sequences); or (iii) fragments of (i) or (ii) above that have nucleoside hydrolysis activity.

C. Methods of Screening for Antagonists of CD39L3

A number of different screening protocols can be utilized to identify agents that modulate the activity of CD39L3.

Screening can take place using isolated, purified or partially purified reagents. In some embodiments, purified or partially purified CD39L3 (e.g., membrane fractions comprising CD39L3) can be used.

Alternatively, cell-based methods of screening can be used. For example, cells that naturally-express CD39L3 or that recombinantly express CD39L3 can be used. In some embodiments, the cells used are mammalian cells, including but not limited to, human cells. In general terms, the screening methods involve screening a plurality of agents to identify an agent that modulates the activity of CD39L3 by, e.g., binding to and/or inhibiting the activity of, a CD39L3 polypeptide, preventing an inhibitor or activator from binding to CD39L3, increasing association of an inhibitor or activator with CD39L3, or activating or inhibiting expression of CD39L3.

In some embodiments, different enzymes are screened to identify an agent that modulates (e.g., antagonizes) CD39L3, but does not significantly modulate activity of a second enzyme. Thus, CD39L3 antagonists can be screened against other enzymes with similar activities to eliminate candidate antagonists that modulate the activities of the other enzyme(s). Enzymes with activities similar to CD39L3 include, e.g., other ecto-NTPDases aside from CD39L3. Thus, in some embodiments, the CD39L3 antagonists inhibit the activity of CD39L3, but do not significantly inhibit activity of other ATPases. In some embodiments, the CD39L3 antagonists of the invention do not significantly inhibit at least one of NTPDases 1, 2, 4, 5, 6, 7, or 8. Generally in these embodiments, candidate agents that antagonize CD39L3 activity are identified and the identified antagonists are subsequently screened against one or more other enzymes. Candidates that significantly affect the activity of the other enzyme(s) may then be discarded.

1. CD39L3 Binding Assays

Optionally, preliminary screens can be conducted by screening for agents capable of binding to CD39L3, as at least some of the agents so identified are likely CD39L3 modulators. Binding assays are also useful, e.g., for identifying endogenous proteins that interact with CD39L3. For example, antibodies, receptors or other molecules that bind CD39L3 can be identified in binding assays.

Binding assays usually involve contacting a CD39L3 protein with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to CD39L3 or displacement of labeled substrates. The CD39L3 protein utilized in such assays can be naturally expressed, cloned or synthesized.

In addition, mammalian or yeast two-hybrid approaches (see, e.g., Bartel, P. L. et. al. *Methods Enzymol,* 254:241 (1995)) can be used to identify polypeptides or other molecules that interact or bind when expressed together in a cell.

2. Activity

CD39L3 antagonists can be identified by screening for agents that inhibit or reduce an activity of CD39L3. Analysis of CD39L3 polypeptide activity is performed according to general biochemical procedures. Such assays include cell-based assays as well as in vitro assays involving purified or partially purified CD39L3 polypeptides or membrane fractions comprising CD39L3.

In some embodiments, CD39L3 antagonists are identified by screening a plurality of agents (generally in parallel) for the ability to inhibit or reduce CD39L3 activity. The level of CD39L3 activity in a cell or other sample can be determined and compared to a baseline value (e.g., a control value or the CD39L3 activity in a sample not contacted with an agent or the CD39L3 activity in a sample contacted to a different agent).

CD39L3 is an enzyme that hydrolyzes nucleoside triphosphates (e.g., ATP) and diphosphates (e.g., ADP), thereby generating a nucleoside diphosphate or monophosphate, respectively, and free phosphate. Activity of CD39L3 generally requires the presence of a divalent cation such as calcium or magnesium. EctoATPases hydrolyze nucleoside triphosphates and diphosphates with differing preference for these substrates. CD39L3 slightly prefers ATP over ADP with a ratio of about 3:2. See, e.g., Lavoie, et al., *Biochem Pharmacol.* 67(10):1917-26 (2004). Accordingly, the nucleoside hydrolysis activity of CD39L3 can be determined by measuring accumulation of the enzyme products (e.g., free phosphate or a nucleoside diphosphate or monophosphate depending on the substrate) or by measuring the depletion of one or more substrates of the enzyme (e.g., triphosphates and diphosphates). An example of a commercially-available kit to measure free phosphate is the Piper Phosphate Assay Kit™ (Molecular Probes, Inc., Eugene, Oreg.).

One example of an assay used to measure the depletion of ATP by CD39L3 is based on the enzymatic luciferin-luciferase assay. The luciferin-luciferase assay is based on the ability of the firefly enzyme, luciferase, to catalyze the luminescent reaction of luciferin with ATP and oxygen to product light. As the amount of ATP is directly proportional to the light emitted, quantification of the emitted light provides a measure of the amount of ATP.

Other methods used to quantify and/or measure the release of ATP and/or ADP by cells include a wide variety of chromatographic procedures. Such chromatographic methods are well known in the art. For example, liquid chromatographic procedures are commonly used to separate and measure levels of ADP and/ATP.

Additionally, the release of ADP into culture media can be measured by the pyruvate kinase-mediated conversion to ATP.

In some embodiments, cells transiently transfected with CD39L3 are measured for CD39L3 activity in suspension or adhered to the plate, within an isotonic buffer including the cation cofactor, calcium or magnesium. The cells are then contacted to one or more agents and tested for CD39L3 activity. Alternatively, membrane preparations of CD39L3 expressing cells are contacted with the agents and tested for CD39L3 activity.

In some embodiments, CD39L3 nucleotide hydrolysis activity is measured indirectly, e.g., by measuring activity of a protein whose activity is affected by a CD39L3 enzymatic product (i.e., nucleoside diphosphate or monophosphate). Alternatively, CD39L3 activity can be measured indirectly by measuring activity of a protein whose activity is effected by a CD39L3 substrate. For example, CD39L3 substrates are agonists of P2 receptor (e.g., P2X, P2Y, etc.) activity. In other words, CD39L3 and P2 receptors compete for substrates. Thus, increased P2 receptor activity in a reaction mixture or cell-based assay following contact with an agent, compared to a control reaction mixture of cell-based assay lacking the agent indicates that the agent may be an antagonist of CD39L3. P2 receptor activity can be measured in a number of ways including by measuring calcium mobilization triggered by P2 receptor activity. See, e.g., Geschwind, et al., *Biochim Biophys Acta* 1012(1):107-15 (1989); Gendron et al., *Curr Drug Targets* 3(3):229-45 (2002); Fernandez-Alvarez, et al., *Pancreas* 22(1):69-71 (2001). Agents identified through this assay could subsequently be confirmed with a direct assay for CD39L3 if desired.

3. Expression Assays

Screening for a compound that modulates the expression of CD39L3 are also provided. Screening methods generally involve conducting cell-based assays in which test compounds are contacted with one or more cells expressing CD39L3, and then detecting an increase or decrease in CD39L3 expression (either transcript, translation product). Assays can be performed with cells that naturally express CD39L3 or in cells recombinantly altered to express CD39L3.

CD39L3 expression can be detected in a number of different ways. For example, the expression level of CD39L3 in a cell can be determined by probing the mRNA expressed in a cell with a probe that specifically hybridizes with a transcript (or complementary nucleic acid derived therefrom) of CD39L3. Probing can be conducted by lysing the cells and conducting Northern blots or without lysing the cells using in situ-hybridization techniques. Alternatively, CD39L3 protein can be detected using, e.g., immunological methods in which a cell lysate is probed with antibodies that specifically bind to CD39L3.

Other cell-based assays involve reporter assays conducted with cells using standard reporter gene assays. These assays can be performed in either cells that do, or do not, express CD39L3. Some of these assays are conducted with a heterologous nucleic acid construct that includes a CD39L3 promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase; Alton and Vapnek (1979) *Nature* 282:864-869), luciferase, β-galactosidase and alkaline phosphatase (Toh, et al. (1980) *Eur. J. Biochem.* 182:231-238; and Hall et al. (1983) *J. Mol. Appl. Gen.* 2:101).

In these assays, cells harboring the reporter construct are contacted with a test compound. Modulated promoter expression is monitored by detecting the level of a detectable reporter. A number of different kinds of CD39L3 modulators can be identified in this assay. For example, a test compound that inhibits the promoter by binding to it, inhibits the promoter by binding to transcription factors or other regulatory factors, binds to their promoter or triggers a cascade that produces a molecule that inhibits the promoter can be identified. Similarly a test compound that, e.g., activates the promoter by binding to it, activates the promoter by binding to transcription factors or other regulatory factors, binds to their promoter or triggers a cascade that produces a molecule that activates the promoter can also be identified.

The level of expression or activity can be compared to a baseline value. The baseline value can be a value for a control sample or a statistical value that is representative of CD39L3 expression levels for a control population (e.g., lean individuals not having or at risk for Type 2 diabetes) or cells (e.g., tissue culture cells not exposed to a CD39L3 antagonist or agonist). Expression levels can also be determined for cells that do not express CD39L3 as a negative control. Such cells generally are otherwise substantially genetically the same as the test cells.

A variety of different types of cells can be utilized in the reporter assays. Cells that express an endogenous CD39L3 include, e.g., pancreatic islet cells. Cells that do not endogenously express CD39L3 can be prokaryotic or eukaryotic. The eukaryotic cells can be any of the cells typically utilized in generating cells that harbor recombinant nucleic acid constructs. Exemplary eukaryotic cells include, but are not limited to, yeast, and various higher eukaryotic cells, including but not limited to, the HepG2, COS, CHO and HeLa cell lines. Xenopus oocytes can also be used.

Various controls can be conducted to ensure that an observed activity is authentic including running parallel reactions with cells that lack the reporter construct or by not contacting a cell harboring the reporter construct with test compound.

4. Validation

Agents that are initially identified by any of the foregoing screening methods can be further tested to validate the apparent activity and/or determine other biological effects of the agent. In some cases, the identified agent is tested for the ability to effect insulin expression. A variety of insulin expression assays are known in the art and may be employed according to the methods of the invention.

In vitro insulin secretion assays using isolated islet cells (normal or diabetic) can be performed in the presence or absence of the candidate activator. In some embodiments, validation studies are conducted with suitable animal models. The basic format of such methods involves administering a lead compound identified during an initial screen to an animal that serves as a model for humans and then determining if CD39L3 activity and/or insulin secretion is in fact modulated following administration of the CD39L3 antagonist.

To perform insulin secretion assays, islets are isolated from mice or rats by collagenase digestion, ficoll gradient separation, and hand picking. Islets are exposed to a buffer containing insulin secretagogues, such as glucose, potassium chloride or GLP-1, in the presence or absence of the candidate activator, and insulin release into the buffer is measured by ELISA assay.

The animal models utilized in validation studies generally are mammals of any kind. Specific examples of suitable animals include, but are not limited to, primates, mice and rats. For example, monogenic models of diabetes (e.g., ob/ob and db/db mice, Zucker rats and Zucker Diabetic Fatty (ZDF) rats etc.) or polygenic models of diabetes (e.g., a high fat fed mouse model) can be useful for validating CD39L3 modulation and its effect in a diabetic animal.

Ideally, a CD39L3 antagonist enhances insulin secretion only in high glucose conditions (i.e., glucose-stimulated insulin expression). Therefore, in some embodiments, a candidate CD39L3 antagonist reduces hyperglycemia in ZDF rats and db/db mice and does not induce hypoglycemia in either diabetic or control animals.

D. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 or more different compounds are possible using the integrated systems of the invention. In addition, microfluidic approaches to reagent manipulation can be used.

The molecule of interest (e.g., CD39L3 or a cell expressing CD39L3) can be bound to the solid state component, directly or indirectly, via covalent or non covalent linkage.

The invention provides in vitro assays for identifying, in a high throughput format, compounds that can modulate the expression or activity of CD39L3. Control reactions that measure CD39L3 activity of the cell in a reaction that does not include a potential modulator are optional, as the assays are highly uniform. Such optional control reactions are appropriate and increase the reliability of the assay. Accordingly, in some embodiments, the methods of the invention include such a control reaction. For each of the assay formats described, "no modulator" control reactions that do not include a modulator provide a background level of binding activity.

In some assays it will be desirable to have positive controls. At least two types of positive controls are appropriate. First, a known activator of CD39L3 of the invention can be incubated with one sample of the assay, and the resulting increase in signal resulting from an increased expression level or activity of CD39L3 are determined according to the methods herein. Second, a known inhibitor of CD39L3 can be added, and the resulting decrease in signal for the expression or activity of CD39L3 can be similarly detected. An example of general ectoATPase antagonist useful in a positive control is the compound ARL 67156. See, e.g., Westfall, et al., *Eur J Pharmacol.* 329(2-3):169-73 (1997).

E. Computer-based Assays

Yet another assay for compounds that modulate the activity of CD39L3 involves computer-assisted drug design, in which a computer system is used to generate a three-dimensional structure of CD39L3 based on the structural information encoded by its amino acid sequence. The input amino acid sequence interacts directly and actively with a pre-established algorithm in a computer program to yield secondary, tertiary, and quaternary structural models of the protein. The models of the protein structure are then examined to identify regions (e.g., the active site) of the structure that have the ability to bind ligands or otherwise be modulated. Similar analyses can be performed on potential receptors or binding partners of CD39L3 and can be used to identify regions of interaction with CD39L3. These regions are then used to identify polypeptides that bind to CD39L3. Once the tertiary structure of a protein of interest has been generated, potential modulators can be identified by the computer system. Three-dimensional structures for potential modulators are generated by entering chemical formulas of compounds. The three-dimensional structure of the potential modulator is then compared to that of CD39L3 to identify binding sites of CD39L3. Binding affinity between the protein and modulators is determined using energy terms to determine which ligands have an enhanced probability of binding to the protein.

III. Administration and Pharmaceutical Compositions

Modulators of CD39L3 (e.g., CD39L3 antagonists) can be administered directly to the mammalian subject in need thereof for modulation of CD39L3 activity in vivo. Individuals in need of inhibition of CD39L3 can include, for example, individuals with type 2 diabetes and pre-diabetic individuals. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences,* 17$^{th}$ ed. 1985)).

CD39L3 antagonists, alone or in combination with other suitable components, can be prepared for injection or for use in a pump device. Pump devices (also known as "insulin pumps") are commonly used to administer insulin to patients and therefore can be easily adapted to include compositions of the present invention. Manufacturers of insulin pumps include Animas, Disetronic and MiniMed.

CD39L3 antagonists, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to induce a beneficial response in the subject over time. The optimal dose level for any patient will depend on a variety of factors including the efficacy of the specific modulator employed, the age, body weight, physical activity, and diet of the patient, on a possible combination with other drugs, and on the severity of the case of diabetes. It is recommended that the daily dosage of the modulator be determined for each individual patient by those skilled in the art in a similar way as for known insulin compositions. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, CD39L3 antagonists of the present invention can be administered at a rate determined by the LD-50 of the modulator, and the side-effects of the modulator at various concentrations, as applied to the mass and overall health of the subject. Administration can be accomplished via single or divided doses.

The compounds of the present invention can also be used effectively in combination with one or more additional active agents depending on the desired target therapy (see, e.g., Turner, N. et al. *Prog. Drug Res.* (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165-71; United Kingdom Prospective Diabetes Study Group: UKPDS 28, *Diabetes Care* (1998) 21: 87-92; Bardin, C. W., (ed.), *Current Therapy In Endocrinology And Metabolism,* 6th Edition (Mosby—Year Book, Inc., St. Louis, Mo. 1997); Chiasson, J. et al., *Ann. Intern. Med.* (1994) 121: 928-935; Coniff, R. et al., *Clin. Ther.* (1997) 19: 16-26; Coniff, R. et al., *Am. J. Med.* (1995) 98: 443-451; and Iwamoto, Y. et al., *Diabet. Med.* (1996) 13 365-370; Kwiterovich, P. Am. *J. Cardiol* (1998) 82(12A): 3U-17U). These studies indicate that modulation of diabetes, among other diseases, can be further improved by the addition of a second agent to the therapeutic regimen. Combination therapy includes administration of a single pharmaceutical dosage formulation that contains a CD39L3 modulator of the invention and one or more additional active agents, as well as administration of a CD39L3 modulator and each active agent in its own separate pharmaceutical dosage formulation. For example, a CD39L3 modulator and a thiazolidinedione can be administered to the human subject together in a single oral dosage composition, such as a tablet or capsule, or each agent can be administered in separate oral dosage formulations. Where separate dosage formulations are used, a CD39L3 modulator and one or more additional active agents can be administered at essentially the same time (i.e., concurrently), or at separately staggered times (i.e., sequentially). Combination therapy is understood to include all these regimens.

One example of combination therapy can be seen in modulating diabetes (or treating diabetes and its related symptoms, complications, and disorders), wherein the CD39L3 modulators can be effectively used in combination with, for example, sulfonylureas (such as chlorpropamide, tolbutamide, acetohexamide, tolazamide, glyburide, gliclazide, glynase, glimepiride, and glipizide); biguanides (such as metformin); a PPAR beta delta agonist; a ligand or agonist of PPAR gamma such as thiazolidinediones (such as ciglitazone, pioglitazone (see, e.g., U.S. Pat. No. 6,218,409), troglitazone, and rosiglitazone (see, e.g., U.S. Pat. No. 5,859,037)); PPAR alpha agonists such as clofibrate, gemfibrozil, fenofibrate, ciprofibrate, and bezafibrate; dehydroepiandrosterone (also referred to as DHEA or its conjugated sulphate ester, DHEA-$SO_4$); antiglucocorticoids; TNFα inhibitors; α-glucosidase inhibitors (such as acarbose, miglitol, and voglibose); amylin and amylin derivatives (such as pramlintide, (see, also, U.S. Pat. Nos. 5,902,726; 5,124,314; 5,175,145 and 6,143,718.)); insulin secretogogues (such as repaglinide, gliquidone, and nateglinide (see, also, U.S. Pat. Nos. 6,251,856; 6,251,865; 6,221,633; 6,174,856)), and insulin.

IV. Determination of β-Cell Mass and Function

The present invention also provides methods of determining β-cell mass or β-cell-specific function in an individual. β-cell specific functions include, e.g., glucose-dependent secretion of insulin and expression of other polypeptides such as amylin. Such determinations are useful for, e.g., diagnosing diabetes or a predisposition of at least some of the pathologies of type 2 diabetes. In other embodiments, expression of CD39L3 is used as an indicator that a stem cell population has β-cell like properties.

As CD39L3 is expressed in insulin-producing β-cells, CD39L3 activity or expression levels in an individual is an indicator of β-cell mass and/or function in an individual. Diagnosis can involve determining the level of CD39L3 in a patient and then comparing the level to a baseline or range. Typically, the baseline value is representative of CD39L3 levels in a lean (i.e., non-diabetic and typically healthy) person or in the patient at a different time (e.g., before treatment or before development of diabetes or manifestation of a diabetes-related symptom). For example, low levels of CD39L3 compared to a baseline range based on expression or activity in a lean, non-diabetic, healthy person(s) indicates that the individual is either Type I diabetic or at risk of developing at least some of the pathologies of Type I diabetes. High levels of CD39L3 compared to a baseline range indicates that the individual is either Type II diabetic or at risk of developing at least some of the pathologies of Type II diabetes. In some embodiments, the level of CD39L3 are measured by taking a blood, urine or tissue sample from a patient and measuring the amount of CD39L3, or a specific fragment thereof (e.g., a fragment that is sufficiently large to distinguish from protein fragments of other unrelated proteins) in the sample using any number of detection methods, such as those discussed herein. In some embodiments, fasting and fed blood or urine levels can be tested.

In some embodiments, the level of CD39L3 activity or expression in a sample is determined and compared to a baseline value of a lean person or persons (or alternatively, of diabetic persons). Alternatively, the level of CD39L3 activity or expression is determined for the same individual at more than one time points, e.g., a day, a week and month, a year or longer apart. Modulation of CD39L3 activity or expression between samples indicates the development of diabetes or a predisposition to develop diabetes. In some embodiments, the baseline level and the level in a sample from an individual, or at least two samples from an individual differ by at least about 5%, 10%, 20%, 50%, 75%, 100%, 200%, 500%, 1000% or more. In some embodiments, the sample from the individual is greater by at least one of the above-listed percentages relative to the baseline level. In some embodiments, the sample from the individual is lower by at least one of the above-listed percentages relative to the baseline level. Similarly, the level in a sample taken from an individual some time period after a first sample was taken can be higher or lower than the level in the first sample.

In some embodiments, the level of CD39L3 in blood or urine is used to monitor the effectiveness of anti-diabetic therapies such as thiazolidinediones, metformin, sulfonylureas and other standard therapies. In some embodiments the activity or expression of CD39L3 will be measured prior to and after treatment of diabetic or insulin resistant patients with anti-diabetic therapies as a surrogate marker of clinical effectiveness. For example, the greater the decrease in CD39L3 expression or activity following treatment, the greater effectiveness of the drug is indicated.

In some embodiments, CD39L3 is detected in an intact individual. In these embodiments, a detectably-labeled reagent that specifically binds to CD39L3 is administered to an individual, allowed time to circulate through the body of the individual and then detected. For example, in some embodiments, in vivo imaging techniques are used to visualize the presence and quantity of CD39L3 in an animal (e.g., a human or non-human mammal). The in vivo imaging methods of the present invention are useful in the diagnosis of diabetes.

In some embodiments, CD39L3 is detected using a labeled reagent such as a labeled antibody specific for CD39L3. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection.

In some embodiments, reagents (e.g., antibodies) specific for CD39L3 are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107).

In other embodiments, antibodies are radioactively labeled. See, e.g., Sumerdon et al., *Nucl. Med. Biol* 17:247-254 (1990); Griffin et al., *J Clin Onc* 9:631-640 (1991); Lauffer, *Magnetic Resonance in Medicine* 22:339-342 (1991)). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

A useful method of labeling antibodies with such radiometals is by means of a bifunctional chelating agent, such as diethylenetriaminepenta-acetic acid (DTPA), as described, for example, by Khaw et al. (*Science* 209:295 (1980)) for In-111 and Tc-99m, and by Scheinberg et al. (*Science* 215: 1511 (1982)). Other chelating agents may also be used.

In still further embodiments, in vivo biophotonic imaging (Xenogen, Almeda, Calif.) is utilized for in vivo imaging.

EXAMPLES

Example 1

This example demonstrates that expression of CD39L3 inhibits glucose-stimulated insulin secretion in β-cells.

Figure 2:
FIG. 2 illustrates an RT-PCR analysis showing the presence of CD39L3 in human RNA samples for β-cells, islets, and brain. Expression of CD39L3 was not detected in human samples of pancreas, liver, kidney, skeletal muscle, brain, and spleen.

CD39L3 mRNA expression was determined in mice. The mouse expression analysis showed this protein to be expressed highly in islets, βHC9 cells, and in thyroid gland (FIG. 1). The human expression analysis with the available mRNAs showed high expression in beta cells, islets, and brain (FIG. 2).

Figure 3:
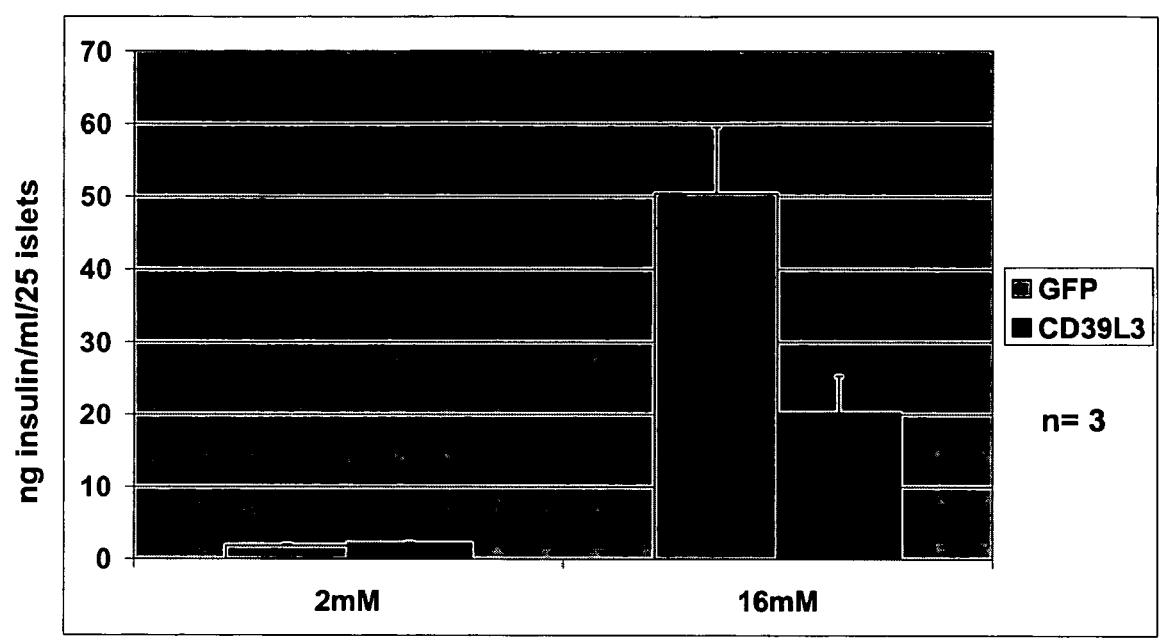
FIG. 3 illustrates results of a static insulin secretion assay of isolated rat islets examined for insulin secretion effect with the over-expression of human CD39L3. CD39L3 and GFP control adenoviruses were infected into rat islets (n=3). Isolated rat islets, infected with CD39L3 adenovirus, showed attenuated glucose dependent insulin secretion compared to GFP adenovirus control.

Human CD39L3 and GFP control adenoviruses were infected into rat islets (n=3). Isolated rat islets, infected with CD39L3 adenovirus, showed attenuated glucose dependent insulin secretion compared to GFP adenovirus control. Thus, it was shown that over-expression of CD39L3 caused an impaired response of the isolated islets to glucose and KCl to insulin secretion. In addition, the attenuated effect of CD39L3 on insulin secretion by over 50% was observed under high (16 mM) glucose (FIG. 3). These results demonstrate the negative effect of CD39L3 on islet cell insulin production, thereby providing a rationale to find a CD39L3 inhibitor in order to improve diabetic status.

Example 2

This example demonstrates a method for assaying CD39L3 nucleotide hydrolysis activity.

As the activity of CD39L3 involves the hydrolysis of nucleoside triphosphates and diphosphates, Molecular Probes' P$_i$per Phosphate Assay Kit™, which is an assay that detects free phosphate, a product of the hydrolysis, was used.

Cells were transiently transfected with the full length human CD39L3 clone were measured for nucleotide hydrolysis activity in suspension or adhered to the plate, within an isotonic buffer including the required cation cofactor, calcium or magnesium. Batches of transiently transfected CD39L3 cells were produced and frozen until use. These cells retain their activity even after freezing and thawing.

Figure 4:
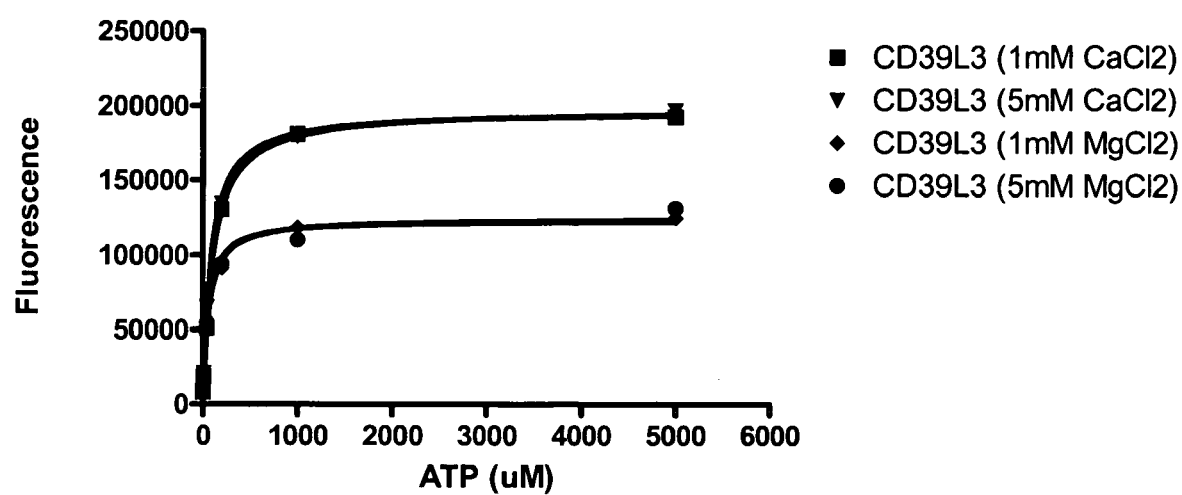
FIG. 4 illustrates the Km of ATP determined for full length human CD39L3 in transiently transfected HEK293 cells. The Km of ATP values determined under two concentrations of each cation source: $CaCl_2$ and $MgCl_2$. [Km=105 μM (1 mM $CaCl_2$); Km=60 μM (1 mM $MgCl_2$); Km=85 μM (5 mM $CaCl_2$); Km=52 μM (5 mM $MgCl_2$)] Activity assays were performed with the Piper Phosphate Assay (Molecular Probes).
Figure 5:
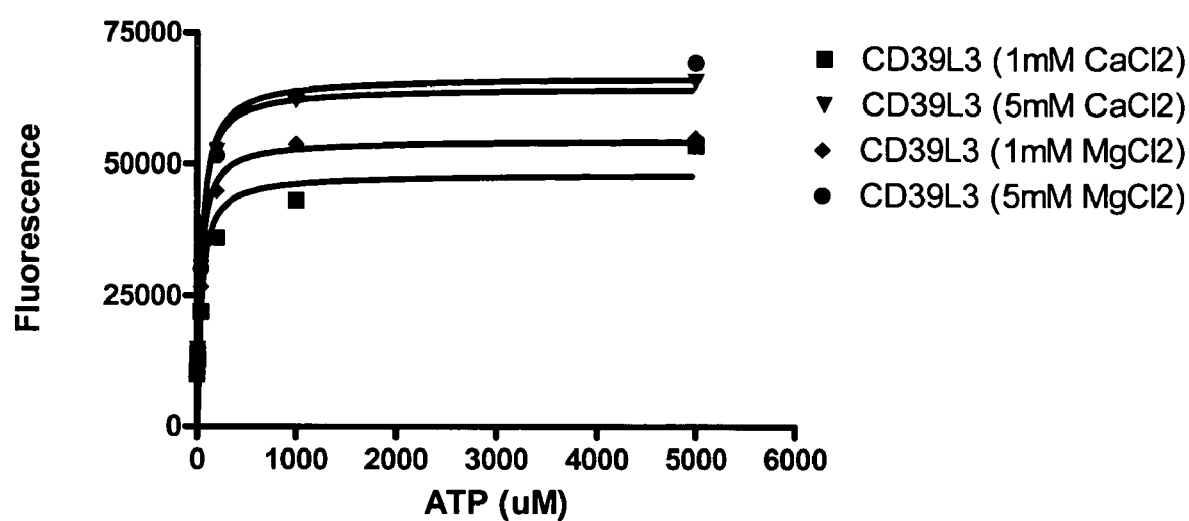
FIG. 5 illustrates the Km of ADP determined for full length human CD39L3 in transiently transfected HEK293 cells. The Km of ADP values determined under two concentrations of each cation source: $CaCl_2$ and $MgCl_2$. [Km=42 uM (1 mM $CaCl_2$); Km=35 μM (1 mM $MgCl_2$); Km=39 μM (5 mM $CaCl_2$); Km=44 μM (5 mM $MgCl_2$)] Activity assays were performed with the Piper Phosphate Assay (Invitrogen).
Figure 6:
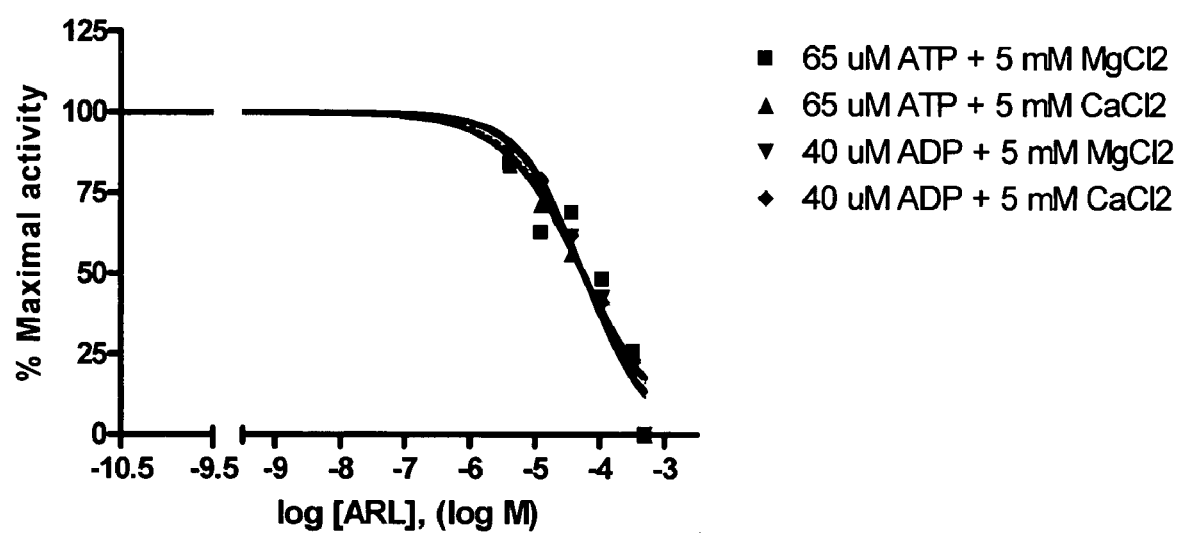
FIG. 6 illustrates the inhibition of CD39L3 examined with the general ectoATPase inhibitor, ARL 67156. HEK293 cells were transiently transfected with full length human CD39L3. The calculations were as follows: IC50=49 uM (65 μM ATP+5 mM $CaCl_2$); IC50=59 μM (65 uM ATP+5 mM $MgCl_2$); IC50=59 μM (40 uM ADP+5 mM $CaCl_2$); IC50=57 μM (40 uM ADP+5 mM $MgCl_2$). Activity assays were performed with the Piper Phosphate Assay (Molecular Probes).

Using cells that were frozen and thawed, the Piper Phosphate Assay was used to determine the Km of ATP and ADP for the full length human CD39L3 clone (FIGS. 4 and 5). In addition, to validate the detection of an inhibitor with this assay format, a general ectoATPase inhibitor, ARL 67156, was examined. This Piper Phosphate Assay detected the inhibition of CD39L3 by ARL 67156 (FIG. 6) using near Km values of substrates (ATP and ADP).

This example demonstrates that CD39L3 activity, and its inhibition with small molecules, can be readily assayed.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for identifying an agent for treating a diabetic or pre-diabetic individual, the method comprising the steps of:
   (i) contacting an agent to a CD39L3 polypeptide at least 95% identical to SEQ ID NO:2, wherein the polypeptide has nucleotide hydrolysis activity;
   (ii) selecting an agent that reduces the activity of the polypeptide; and
   (iii) testing the effect of the selected agent on glucose-stimulated insulin expression of a cell, thereby identifying an agent for treating a diabetic or pre-diabetic individual.

2. The method of claim 1, wherein the polypeptide is expressed on a cell and the contacting step (i) comprises contacting the cell with the agent.

3. The method of claim 1, wherein a membrane fraction comprises the polypeptide.

4. The method of claim 1, wherein the activity of the polypeptide is measured by detecting free phosphate in the mixture.

5. The method of claim 1, wherein the polypeptide comprises SEQ ID NO:2.

6. The method of claim 1, wherein the method further comprises testing the effect of the selected agent on the activity of a second ectoATPase other than CD39L3 and selecting an agent that does not reduce the activity of the second ectoATPase.

* * * * *

SEQUENCE LISTING

```
<160> NUMBER OF SEQ ID NOS: 2

<210> SEQ ID NO 1
<211> LENGTH: 1590
<212> TYPE: DNA
<213> ORGANISM: Homo sapiens
<220> FEATURE:
<223> OTHER INFORMATION: human CD39L3 cDNA

<400> SEQUENCE: 1
atgttcactg tgctgacccg ccaaccatgt gagcaagcag gcctcaaggc cctctaccga      60
actccaacca tcattgcctt ggtggtcttg cttgtgagta ttgtggtact tgtgagtatc     120
actgtcatcc agatccacaa gcaagaggtc ctccctccag gactgaagta tggtattgtg     180
ctggatgccg ggtcttcaag aaccacagtc tacgtgtatc aatggccagc agaaaaagag     240
aataataccg gagtggtcag tcaaaccttc aaatgtagtg tgaaaggctc tggaatctcc     300
agctatggaa ataaccccca agatgtcccc agagcctttg aggagtgtat gcaaaaagtc     360 aagggcagg ttccatccca cctccacgga tccacccca ttcacctggg agccacggct      420
gggatgcgct tgctgaggtt gcaaaatgaa acagcagcta atgaagtcct tgaaagcatc     480
caaagctact tcaagtccca gcccttgac tttaggggtg ctcaaatcat ttctgggcaa     540
gaagaagggg tatatggatg gattacagcc aactatttaa tgggaaattt cctggagaag     600
```

-continued

```
aacctgtggc acatgtgggt gcacccgcat ggagtggaaa ccacgggtgc cctggactta    660
ggtggtgcct ccacccaaat atccttcgtg gcaggagaga agatggatct gaacaccagc    720
gacatcatgc aggtgtccct gtatggctac gtatacacgc tctacacaca cagcttccag    780
tgctatggcc ggaatgaggc tgagaagaag tttctggcaa tgctcctgca gaattctcct    840
accaaaaacc atctcaccaa tccctgttac cctcgggatt atagcatcag cttcaccatg    900
ggccatgtat ttgatagcct gtgcactgtg gaccagaggc cagaaagtta taaccccaat    960
gatgtcatca cttttgaagg aactggggac ccatctctgt gtaaggagaa ggtggcttcc   1020
atatttgact tcaaagcttg ccatgatcaa gaaacctgtt cttttgatgg ggtttatcag   1080
ccaaagatta aagggccatt tgtggctttt gcaggattct actacacagc cagtgctta    1140
aatctttcag gtagcttttc cctggacacc ttcaactcca gcacctggaa tttctgctca   1200
cagaattgga gtcagctccc actgctgctc cccaaatttg atgaggtata tgcccgctct   1260
tactgcttct cagccaacta catctaccac ttgtttgtga acggttacaa attcacagag   1320
gagacttggc cccaaatca cttgaaaaaa gaagtgggga atagcagcat agcctggtct   1380
cttggctaca tgctcagcct gaccaaccag atcccagctg aaagccctct gatccgtctg   1440
cccatagaac cacctgtctt tgtgggcacc ctcgctttct tcacagtggc agccttgctg   1500
tgtctggcat ttcttgcata cctgtgttca gcaaccagaa gaaagaggca ctccgagcat   1560
gcctttgacc atgcagtgga ttctgactga                                    1590
```

<210> SEQ ID NO 2
<211> LENGTH: 529
<212> TYPE: PRT
<213> ORGANISM: Homo sapiens
<220> FEATURE:
<223> OTHER INFORMATION: human CD39L3

<400> SEQUENCE: 2

```
Met Phe Thr Val Leu Thr Arg Gln Pro Cys Glu Gln Ala Gly Leu Lys
  1               5                  10                  15

Ala Leu Tyr Arg Thr Pro Thr Ile Ile Ala Leu Val Val Leu Leu Val
                 20                  25                  30

Ser Ile Val Val Leu Val Ser Ile Thr Val Ile Gln Ile His Lys Gln
             35                  40                  45

Glu Val Leu Pro Pro Gly Leu Lys Tyr Gly Ile Val Leu Asp Ala Gly
         50                  55                  60

Ser Ser Arg Thr Thr Val Tyr Val Tyr Gln Trp Pro Ala Glu Lys Glu
 65                  70                  75                  80

Asn Asn Thr Gly Val Val Ser Gln Thr Phe Lys Cys Ser Val Lys Gly
                 85                  90                  95

Ser Gly Ile Ser Ser Tyr Gly Asn Asn Pro Gln Asp Val Pro Arg Ala
            100                 105                 110

Phe Glu Glu Cys Met Gln Lys Val Lys Gly Gln Val Pro Ser His Leu
        115                 120                 125

His Gly Ser Thr Pro Ile His Leu Gly Ala Thr Ala Gly Met Arg Leu
    130                 135                 140

Leu Arg Leu Gln Asn Glu Thr Ala Ala Asn Glu Val Leu Glu Ser Ile
145                 150                 155                 160

Gln Ser Tyr Phe Lys Ser Gln Pro Phe Asp Phe Arg Gly Ala Gln Ile
                165                 170                 175

Ile Ser Gly Gln Glu Glu Gly Val Tyr Gly Trp Ile Thr Ala Asn Tyr
```

-continued

```
                180                 185                 190
Leu Met Gly Asn Phe Leu Glu Lys Asn Leu Trp His Met Trp Val His
        195                 200                 205
Pro His Gly Val Glu Thr Thr Gly Ala Leu Asp Leu Gly Gly Ala Ser
        210                 215                 220
Thr Gln Ile Ser Phe Val Ala Gly Glu Lys Met Asp Leu Asn Thr Ser
225                 230                 235                 240
Asp Ile Met Gln Val Ser Leu Tyr Gly Tyr Val Tyr Thr Leu Tyr Thr
                245                 250                 255
His Ser Phe Gln Cys Tyr Gly Arg Asn Glu Ala Glu Lys Lys Phe Leu
            260                 265                 270
Ala Met Leu Leu Gln Asn Ser Pro Thr Lys Asn His Leu Thr Asn Pro
        275                 280                 285
Cys Tyr Pro Arg Asp Tyr Ser Ile Ser Phe Thr Met Gly His Val Phe
        290                 295                 300
Asp Ser Leu Cys Thr Val Asp Gln Arg Pro Glu Ser Tyr Asn Pro Asn
305                 310                 315                 320
Asp Val Ile Thr Phe Glu Gly Thr Gly Asp Pro Ser Leu Cys Lys Glu
                325                 330                 335
Lys Val Ala Ser Ile Phe Asp Phe Lys Ala Cys His Asp Gln Glu Thr
                340                 345                 350
Cys Ser Phe Asp Gly Val Tyr Gln Pro Lys Ile Lys Gly Pro Phe Val
            355                 360                 365
Ala Phe Ala Gly Phe Tyr Tyr Thr Ala Ser Ala Leu Asn Leu Ser Gly
        370                 375                 380
Ser Phe Ser Leu Asp Thr Phe Asn Ser Ser Thr Trp Asn Phe Cys Ser
385                 390                 395                 400
Gln Asn Trp Ser Gln Leu Pro Leu Leu Leu Pro Lys Phe Asp Glu Val
                405                 410                 415
Tyr Ala Arg Ser Tyr Cys Phe Ser Ala Asn Tyr Ile Tyr His Leu Phe
                420                 425                 430
Val Asn Gly Tyr Lys Phe Thr Glu Glu Thr Trp Pro Gln Ile His Phe
            435                 440                 445
Glu Lys Glu Val Gly Asn Ser Ser Ile Ala Trp Ser Leu Gly Tyr Met
    450                 455                 460
Leu Ser Leu Thr Asn Gln Ile Pro Ala Glu Ser Pro Leu Ile Arg Leu
465                 470                 475                 480
Pro Ile Glu Pro Pro Val Phe Val Gly Thr Leu Ala Phe Phe Thr Val
                485                 490                 495
Ala Ala Leu Leu Cys Leu Ala Phe Leu Ala Tyr Leu Cys Ser Ala Thr
            500                 505                 510
Arg Arg Lys Arg His Ser Glu His Ala Phe Asp His Ala Val Asp Ser
        515                 520                 525
Asp
```